(12) United States Patent
Rogers

(10) Patent No.: US 7,696,399 B2
(45) Date of Patent: Apr. 13, 2010

(54) SUTURELESS WOUND CLOSURE AND METHOD OF APPLICATION

(76) Inventor: Gary S. Rogers, 45 Dodges Row, Wenham, MA (US) 01984

( * ) Notice: Subject to any disclaimer, the term of this patent is extended or adjusted under 35 U.S.C. 154(b) by 79 days.

(21) Appl. No.: 11/895,036

(22) Filed: Aug. 22, 2007

(65) Prior Publication Data
US 2008/0051687 A1 Feb. 28, 2008

Related U.S. Application Data

(60) Provisional application No. 60/839,555, filed on Aug. 23, 2006.

(51) Int. Cl.
*A61F 13/00* (2006.01)

(52) U.S. Cl. ............... 602/52; 602/42; 602/54; 602/57; 606/213; 606/215; 606/216

(58) Field of Classification Search .......... 602/41–59; 606/213–216, 151; D24/189; 600/562
See application file for complete search history.

(56) References Cited

U.S. PATENT DOCUMENTS

| | | | |
|---|---|---|---|
| 5,176,703 A | 1/1993 | Peterson | |
| 5,534,010 A | 7/1996 | Peterson | |
| 6,007,562 A * | 12/1999 | Harren et al. | 606/213 |
| 6,126,615 A * | 10/2000 | Allen et al. | 600/562 |
| 6,176,868 B1 * | 1/2001 | Detour | 606/215 |
| 6,329,564 B1 | 12/2001 | Lebner | |
| 6,822,133 B2 | 11/2004 | Lebner | |
| 6,831,205 B2 | 12/2004 | Lebner | |
| 2004/0054312 A1 | 3/2004 | Lebner | |
| 2004/0215217 A1 * | 10/2004 | Banbury et al. | 606/151 |
| 2005/0020956 A1 | 1/2005 | Lebner | |
| 2005/0020957 A1 | 1/2005 | Lebner | |
| 2005/0021081 A1 | 1/2005 | Lebner | |
| 2005/0021082 A1 | 1/2005 | Lebner | |
| 2005/0021083 A1 | 1/2005 | Lebner | |
| 2005/0033215 A1 | 2/2005 | Lebner | |
| 2005/0080453 A1 | 4/2005 | Lebner et al. | |

* cited by examiner

*Primary Examiner*—Kim M Lewis
(74) *Attorney, Agent, or Firm*—David M. Driscoll, Esq.

(57) ABSTRACT

A sutureless biopsy closure that includes an adhesive member adapted to be disposed over a biopsy region prior to the performance of the biopsy; at least one adhesive strip including one end supported on the adhesive member and a second free end forming a tab. The tab is adapted to extend over the biopsy region to seal the wound.

7 Claims, 5 Drawing Sheets

SUTURELESS WOUND CLOSURE AND METHOD OF APPLICATION

RELATED APPLICATION

Priority for this application is hereby claimed under 35 U.S.C. §119(e) to commonly owned and co-pending U.S. Provisional Patent Application No. 60/839,555 which was filed on Aug. 23, 2006 and which is incorporated by reference herein in its entirety.

TECHNICAL FIELD

The present invention relates, in general, to an improved sutureless wound closure, and pertains more particularly to a closure for a biopsy site or trocar port site. The present invention also relates to the method of application of the closure relative to the biopsy site or trocar port site. The principles of the present invention may also apply to any other types of wound closure applications.

BACKGROUND OF THE INVENTION

There are existing techniques for taking biopsies and thereafter closing the biopsy incision or wound. There are also existing techniques for closing a trocar port wound. There are drawbacks associated with existing techniques including the need for multiple instruments in performing the biopsy which typically includes sutures, a needle holder and forceps. There is also the potential for a needle stick injury. There is an increased cost of suturing and sterilization of the instruments used. There is also a need for the nurse to place a bandage on the wound following the procedure and the patient must return to have the suture removed.

Another problem associated with current technique, particularly for performing a biopsy, is that once the local anesthesia is administered the skin lesion often disappears due to the infiltration of the anesthetic into the skin. The physician then loses the location of where to take the biopsy. To prevent this, the surgeon often marks the area with a magic-marker prior to infiltrating the anesthetic. However, this requires additional steps in the process.

Accordingly it is an object of the present invention to provide an improved sutureless wound closure and associated method of application.

It is another object of the present invention to provide a wound closure that is preferably applied to the site prior to the biopsy.

It is still another object of the present invention to provide a closure that does not require any separate instruments for application thereof.

It is a further object of the present invention to provide a closure that is relatively inexpensive, easy to apply and does not require subsequent procedures.

SUMMARY OF THE INVENTION

To accomplish the foregoing and other object, features and advantages of the present invention, there is provided a sutureless biopsy closure that comprises a main adhesive member adapted to be disposed over the biopsy region prior to the biopsy step and at least one adhesive strip including one end supported on the adhesive member and a second free end forming a tab. The tab is adapted to extend over the wound region to seal the wound.

In accordance with other aspects of the present invention the sutureless biopsy closure may include a pair of adhesive strips disposed on opposed sides of the biopsy region; the tab may have a removable paper backing; and the pair of adhesive strips may overlap to seal the wound.

The invention also relates to a method of applying a sutureless biopsy closure over a skin lesion comprising the steps of: applying an adhesive member over the skin lesion so as to cover the entire skin lesion; providing at least one adhesive strip supported on the adhesive member and having a free end forming a tab; and moving the free end over the skin wound area after the performance of the biopsy or incision so as to seal the wound.

BRIEF DESCRIPTION OF THE DRAWINGS

Numerous other objects, features and advantages of the present invention should now become apparent upon a reading of the following detailed description taken in conjunction with the accompanying drawings, in which.

DETAILED DESCRIPTION

Figure 1:
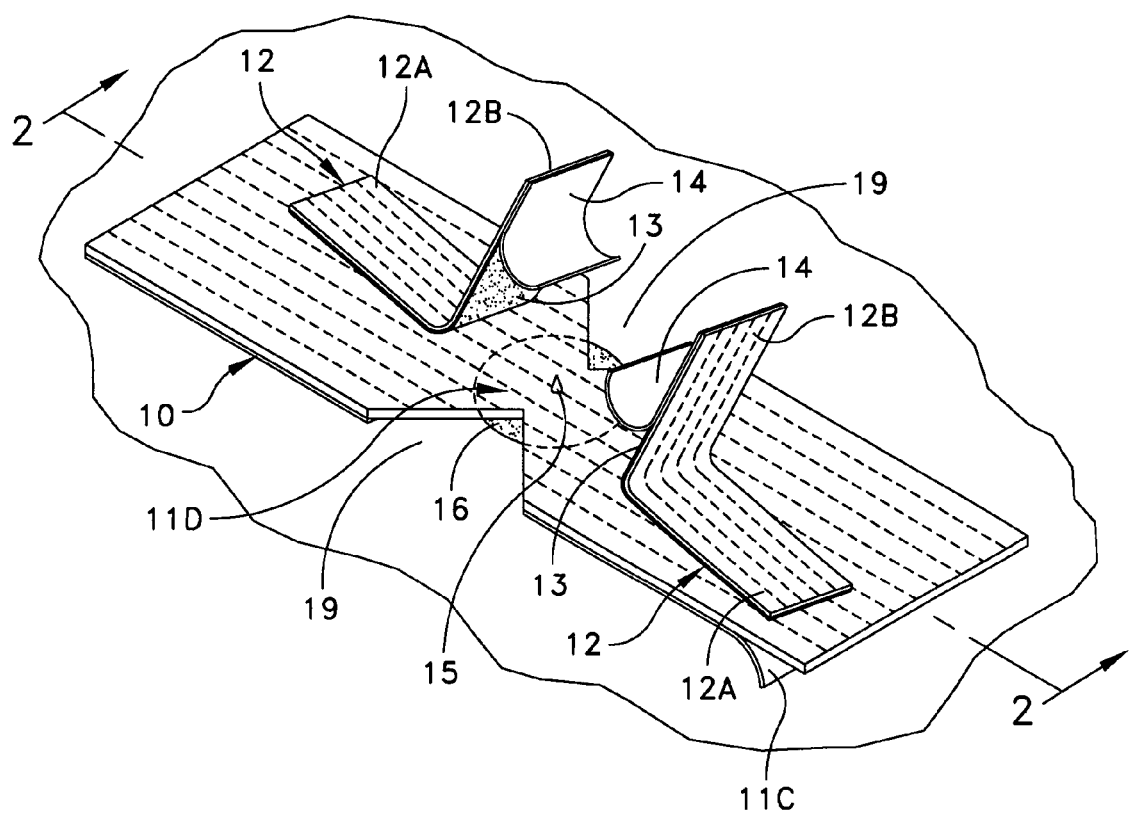
FIG. 1 is a top perspective view of the closure as applied over a skin lesion to be biopsied.
Figure 2:
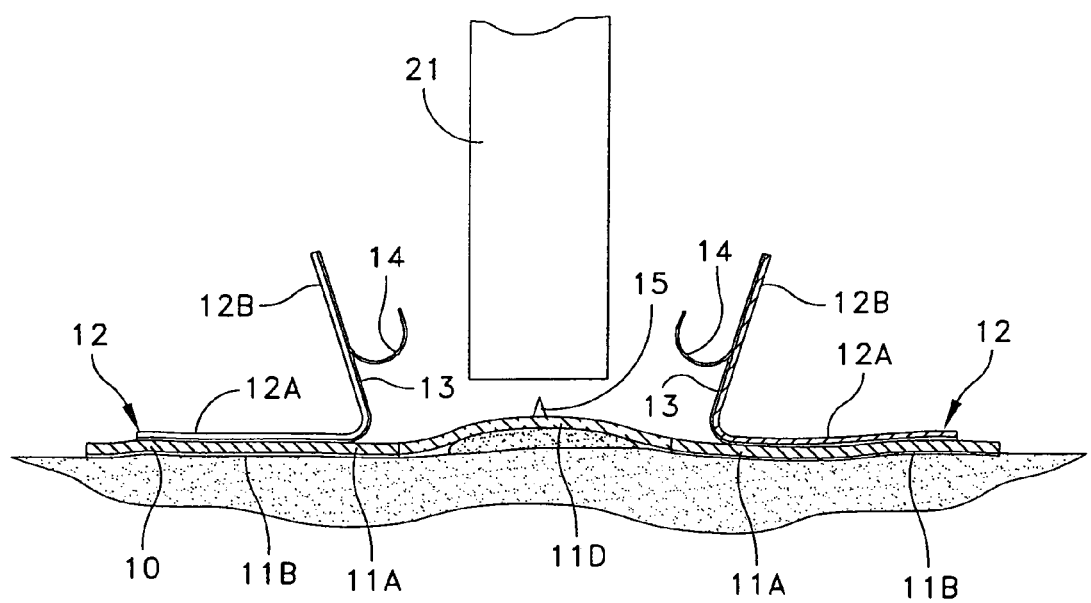
FIG. 2 is a cross sectional side view of the closure of FIG. 1.

Referring now to the drawings, a preferred embodiment of the present invention is illustrated in FIGS. 1-5. FIGS. 1 and 2 illustrate the closure of the present invention which is comprised of a main adhesive member 10. The adhesive member 10 may be a Roclos strip or other conventional adhesive strip material. The adhesive member 10 is preferably comprised of a main flexible plastic layer or film 11A that has an adhesive layer 11B applied thereto, such as illustrated in the cross-sectional view of FIG. 2. The adhesive member 10 also has a central area 11D that may be of different shapes but that is preferably transparent. This transparency allows the surgeon to have ready viewing of the wound area for the proper application of the adhesive member 10.

As also illustrated in FIG. 2, a nubbin 15 is provided on the adhesive member at the transparent area 11D for the purpose of punch registration, as discussed hereinafter. The nubbin 15 is preferably integrally formed at the center of the area 11D and may be a 2 mm×2 mm×2 mm projection of the plastic film that can be easily grabbed with a forceps after the biopsy punch has been engaged. The nubbin functions as a means for lining up the skin area that is to be biopsied. The nubbin 15 functions as a bulls-eye for placing the punch-biopsy instrument 21 over the target skin lesion 16 so there is no question as to where to take the specimen. In this way, there is no need for multiple steps and no need for the use of marking pen (which must be discarded as skin markers are for one use only and then no longer sterile).

The surgeon places the adhesive strip with its transparent area 11D over the area to be biopsied and then infiltrates an anesthetic through the adhesive film into the skin or a topical anesthetic such as EMLA cream 20% benzocaine can be used. The nubbin 15 is essentially the target for the punch biopsy. The nubbin acts as a grabbing point for the forceps to remove the specimen. Normally, the surgeon uses forceps directly grabbing the skin specimen that has been cut using the skin punch. Grabbing the skin directly results in crushing the specimen. This can render the biopsy unreadable for histological diagnosis. However, with the technique of the present invention the surgeon simply grabs the nubbin with forceps or the like and in that way easily and effectively takes a clean biopsy specimen.

As can be seen in FIG. 1, the adhesive member 10 is generally rectangular, but includes a constricted center section that is V-shaped as shown at 19 in FIG. 1. This V-shaped center section allows the same size adhesive member 10 to be used regardless of the size of the biopsy skin punch 21 which typically is in a range of 2 mm-6 mm. The V-shape is actually a double V-shape as illustrated in FIG. 1 forming a constriction, the symmetric center of which is aligned with the center of the lesion or wound area 16.

The adhesive member 10, as indicated before is comprised of a main layer 11A and an adhesive layer 11B. As also illustrated in FIG. 1 it is preferred to have a peel away strip 11C attached to the adhesive member that can be peeled off to expose the adhesive layer 11B. The adhesive layer, because it has contact primarily only with the skin area about the lesion can be an aggressive adhesive substance. The adhesive may be a standard cyanoacrylate as is used in conventional skin bandages, including steri-strips such as made by 3M or other adhesive bandages such as made by J&J. It is preferred that a latex based adhesive not be used due to the possible risk of contact dermatitis.

Attached to the member 10 is a pair of adhesive strips 12. Each strip has one end 12A that is fixed to the adhesive member 10 and a free end 12B that has an outer adhesive layer 13 covered by a removable paper backing 14. The main adhesive member 10 is placed over the lesion or wound region 16 such as in the position illustrated in FIG. 1. In that position the paper backing 14 remains on the free ends 12B of the adhesive strips 12.

The adhesive member 10 is preferably constructed of a soft and flexible adhesive strip. The strips 12 on the other hand are preferably stiffer and more rigid than the main member 10. The adhesive layer 11B maybe impregnated with an antimicrobial to sterilize the incision site on the skin or may be impregnated with a topical anesthetic so injection of anesthesia is not needed.

One of the advantages of the present closure system is that the closure is placed on the dry skin before the biopsy is taken. In that way there is no body fluid such as blood that could otherwise interfere with the bonding of the closure adhesive to the stratum corneum (top skin layer). In other words the main adhesive member is not applied to an open wound area. As such it is preferred that the transparent area 11D be free of any adhesive material. As far as the other adhesive layers are concerned preferably the layer 11B is a more aggressive adhesive than the layers 13, although one of the layers 13 can be an aggressive adhesive, the one that overlaps the other strip 12.

Figure 3:
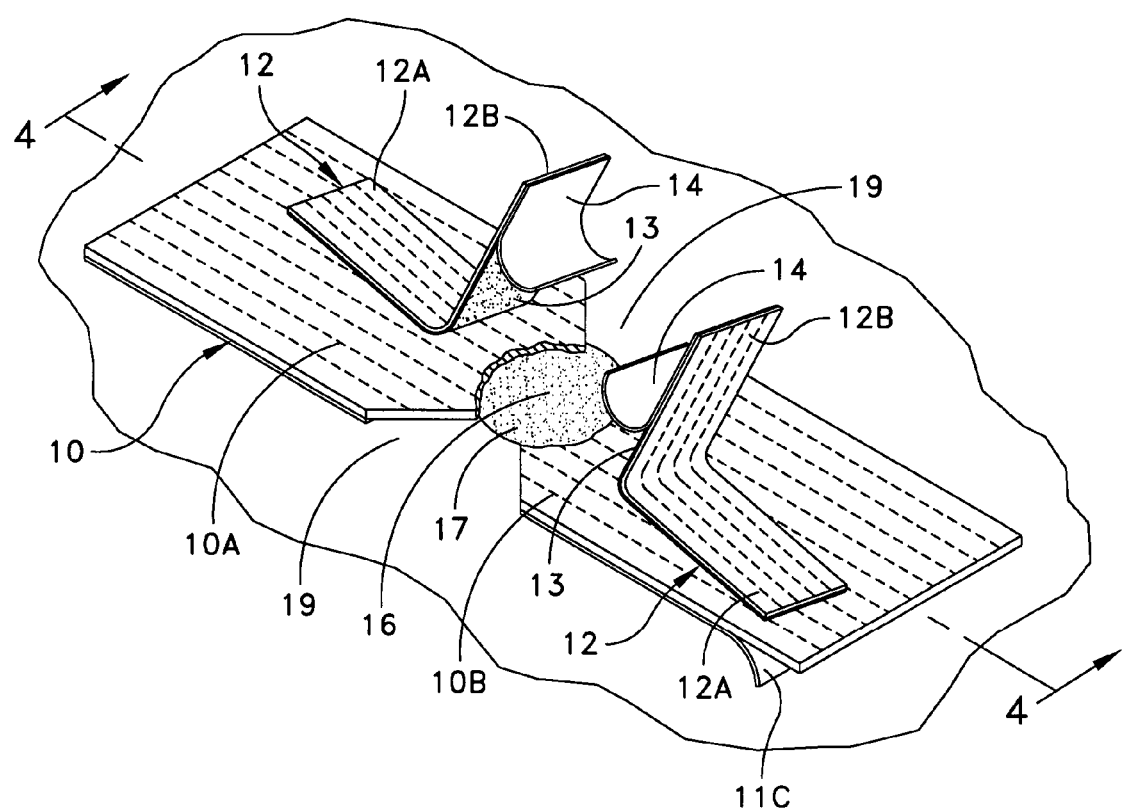
FIG. 3 is a top perspective view of the closure after the biopsy has occurred.

FIG. 3 illustrates the next step in which a biopsy has been taken at the region 16, removing part of the adhesive member 10 as illustrated at 17 in FIG. 3. This leaves two separated portions 10A and 10B of the adhesive member 10. As noted in FIG. 3 the punch action separates the adhesive member. This step also automatically locates the edge of opening 17 directly at the wound margin. This, in turn, permits precise skin closure. In this regard, prior art systems required careful placement of the adhesive strip because they applied the strip after the biopsy was performed and had to thus deal with a placement at the edge of a bleeding wound, which is not at all desirable.

Figure 4:
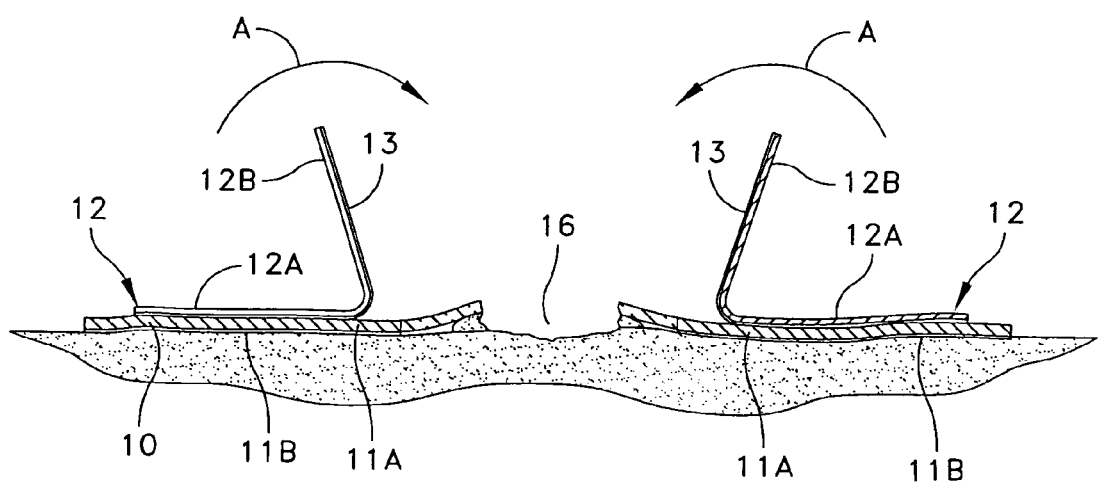
FIG. 4 is a cross sectional view similar to that shown in FIG. 2 but with the removable paper backing removed after the biopsy has occurred.
Figure 5:
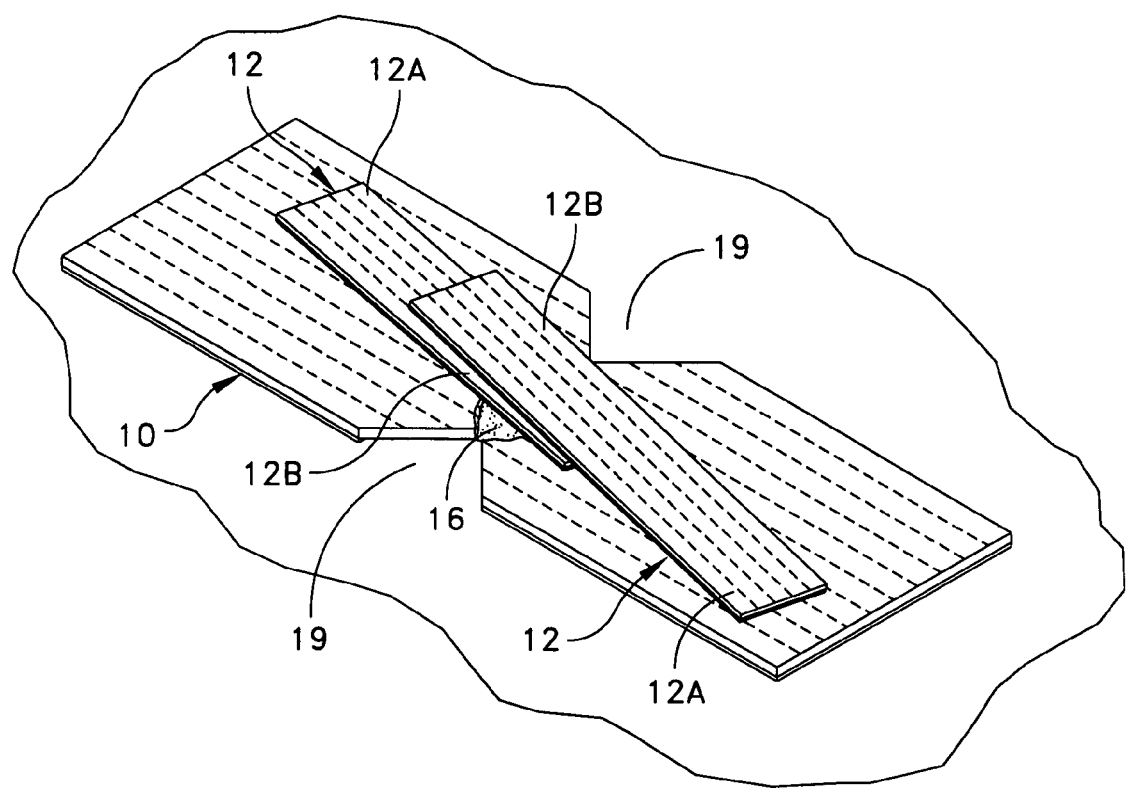
FIG. 5 is a top perspective view of the closure in a final step sealing the wound.

FIG. 4 illustrates the next step in which the paper backing 14 has been removed to expose the adhesive layer 13. FIG. 4 illustrates the opposed adhesive layers 13 on either side of the region 16. The next step in the sequence is to fold the free ends 12B in the direction of arrows A in FIG. 4 so that they are disposed over the biopsy region 16 in an overlapping manner. In this regard refer also to FIG. 5 that shows the free ends 12B overlapping over the region 16. At least one of the free ends 12B extends completely over the region 16. In a preferred embodiment, both of the free ends extend completely over the region 16, as illustrated in FIG. 5. It is preferred that, when the free ends 12B are moved in the direction of arrows A in FIG. 4 that some small amount of tension is applied to them so that there is a downward pressure at the biopsy region 16 so as to provide a proper seal about that area. The backing paper 14 preferably breaks from the strip 12 with the gloved hand preferably never touching the adhesive. This prevents the strip from sticking to the finger of the user.

One advantage of the closure of the present invention is that the closure can be readily applied on to the dry skin surface before the wound or incision is made. In this way the attachment of the closure is made in a clean and secure manner. The cut can then be made directly through the strip, such as with a biopsy punch or trocar. Once the closure is in place, then the cutting step creates two separate strip segments that are aligned at the margin of the wound. This allows the skin edges to thus line up when the wound is closed, avoiding a "step" from one edge to another. When the biopsy has been performed the surgeon can then easily remove the specimen by grasping the nubbin that holds the specimen. The nubbin and portion of the adhesive member that have been punched out can be later discarded. When the specimen is originally taken by means of the biopsy punch, this extracts not only the specimen but also a portion of the transparent film and nubbin that are punched therewith. As indicated before a forceps can be used for removing the nubbin and portion of transparent film.

Another advantage of the closure of the present invention is that the closure tabs or strips 12 do not close against the skin, but instead close against the main strip material 10. In this way an aggressive bonding agent can be used between the tabs and main adhesive strip. There is thus no need to have skin biosafety, i.e. a permanent bonding agent can thus be used. A sterile collagen powder may also be added to the aggressive adhesive in the event that any blood leakage occurs at the wound site to facilitate hemostasis.

Having now described a limited number of embodiments of the present invention, it should now become apparent to one skilled in the art that numerous other embodiments and modifications thereof are contemplated as falling within the scope of the present invention as defined by the appended claims. For example, although in a preferred embodiment a pair of opposed adhesive strips are employed, in an alternate embodiment of the invention a single, longer adhesive strip may also be employed with a free end that is adapted to properly cover the entire biopsy region 16. The wound closure of the present invention can be used for biopsy purposes, but can also be used for the effective closure of other types of wounds such as provided by the usual incision made for endoscopic or laparoscopic procedures. For example, the closure can be used to cover a trocar port.

What is claimed is:

1. A method of applying a suture-less wound closure device over a target skin area that includes a wound site, and in which the suture-less wound closure device is comprised of a thin adhesive member that includes a main flexible layer and an adhesive layer that is applied to the main flexible layer, the thin adhesive member having a length and width and opposed first and second sides at the opposite ends of the length thereof, the adhesive member further having a constricted width transparent intermediate area between the opposed sides thereof defining a minimum width of the thin adhesive member, the adhesive layer that is adhered to the main flexible layer extending over most of the area of the main flexible layer but terminating short of the constricted width transparent intermediate area so that the intermediate area is free of the adhesive layer, a pair of oppositely disposed adhesive strips including first and second adhesive strips and each having a secured end and a free end, the adhesive strips having their free ends directed toward each other and each having an unfolded position and a folded position, said method comprising the steps of:

attaching the secured ends of the first and second adhesive strips at the respective opposed first and second sides of the adhesive member, the free ends of the adhesive strips each including a removable backing that initially prevents attachment of the free ends;

applying the thin adhesive member over the wound so that the adhesive layer thereof secures the adhesive member over the wound while the adhesive strips are in the folded position;

while applying the adhesive member, aligning the constricted width transparent intermediate area over the wound site whereby the transparent intermediate area permits observation of the wound site while applying the adhesive member;

punching the skin by using a biopsy skin punch at the constricted width transparent intermediate area to remove at least a part of the transparent intermediate area and a biopsy sample, the step of punching the skin using a biopsy skin punch separating the adhesive member into two separate and spaced apart adhesive member portions;

removing the backing from the free end of each of the adhesive strips;

joining the two separate and spaced apart adhesive member portions by unfolding the first adhesive strip of the pair of adhesive strips over the wound site with the free end thereof attached to the second side of the adhesive member; and unfolding the second adhesive strip of the pair of adhesive strips over the wound site with the free end thereof attached over the first side of the adhesive member.

2. The method of claim 1 wherein the second adhesive strip is attached to the top of the first adhesive strip as the second adhesive strip is unfolded.

3. The method of claim 1 wherein the constricted area has a V-shape.

4. The method of claim 3 wherein the constricted area has a double V-shape.

5. A suture-less wound closure device for use over a target skin area that includes a wound site, and in which the suture-less wound closure device is comprised of a thin adhesive member that includes a main flexible layer and an adhesive layer that is applied to the main flexible layer, the thin adhesive member having a length and width and opposed first and second sides at the opposite ends of the length thereof, the adhesive member also having a length and width that are both an order of magnitude greater than the thickness thereof, the adhesive member further having a constricted width transparent intermediate area between the opposed sides thereof defining a minimum width of the thin adhesive member, the adhesive layer that is adhered to the main flexible layer extending over most of the area of the main flexible layer but terminating short of the constricted width transparent intermediate area so that the intermediate area is free of the adhesive layer, a pair of oppositely disposed adhesive strips including first and second adhesive strips and each having a secured end and a free end, the adhesive strips having their free ends directed toward each other and each having an unfolded position and a folded position, the secured ends of the first and second adhesive strips attached at the respective opposed first and second sides of the adhesive member, the free ends of the adhesive strips each including a removable backing that initially prevents attachment of the free ends, the thin adhesive member adapted to be disposed over the wound so that the adhesive layer thereof secures the adhesive member over the wound while the adhesive strips are in the folded position, while applying the adhesive member, the constricted width transparent intermediate area is aligned over the wound site whereby the transparent intermediate area permits observation of the wound site while applying the adhesive member, a biopsy skin punch is used to punch the constricted width transparent intermediate area to remove at least a part of the transparent intermediate area and a biopsy sample, the punching of the skin using a biopsy skin punch separates the adhesive member into two separate and spaced apart adhesive member portions, the backing from the free end of each of the adhesive strips being removed so that the strips can be moved to an unfolded position, using the adhesive strips to join the two separate and spaced apart adhesive member portions by unfolding the first adhesive strip of the pair of adhesive strips over the wound site with the free end thereof attached to the second side of the adhesive member, and unfolding the second adhesive strip of the pair of adhesive strips over the wound site with the free end thereof attached over the first side of the adhesive member.

6. The closure device of claim 5 wherein the constricted area has a V-shape.

7. The closure of claim 6 wherein the constricted area has a double V-shape.

* * * * *